United States Patent
Morris

(10) Patent No.: US 9,795,676 B2
(45) Date of Patent: Oct. 24, 2017

(54) CHROMIUM 4-HYDROXYISOLEUCINATE COMPOUND METHODS FOR PREPARTION AND USE

(71) Applicant: Shayne Kenneth Morris, Ogden, UT (US)

(72) Inventor: Shayne Kenneth Morris, Ogden, UT (US)

(*) Notice: Subject to any disclaimer, the term of this patent is extended or adjusted under 35 U.S.C. 154(b) by 329 days.

(21) Appl. No.: 14/637,239

(22) Filed: Mar. 3, 2015

(65) Prior Publication Data
US 2015/0246870 A1    Sep. 3, 2015

Related U.S. Application Data

(60) Provisional application No. 61/947,103, filed on Mar. 3, 2014.

(51) Int. Cl.
| | | |
|---|---|---|
| *A61K 36/53* | (2006.01) | |
| *C12P 13/12* | (2006.01) | |
| *A61K 45/06* | (2006.01) | |
| *A61K 31/28* | (2006.01) | |
| *C07C 227/18* | (2006.01) | |

(52) U.S. Cl.
CPC .............. *A61K 45/06* (2013.01); *A61K 31/28* (2013.01); *C07C 227/18* (2013.01)

(58) Field of Classification Search
None
See application file for complete search history.

(56) References Cited

U.S. PATENT DOCUMENTS

| | | | |
|---|---|---|---|
| 6,903,136 B2 * | 6/2005 | Miller | A23L 33/175 424/646 |
| 8,771,755 B2 | 7/2014 | Gojon-Romanillos et al. | |
| 2002/0058071 A1 | 5/2002 | Siskind | |
| 2004/0071825 A1 * | 4/2004 | Lockwood | A23L 2/395 426/72 |
| 2005/0226948 A1 * | 10/2005 | Lee | A61K 31/198 424/757 |
| 2005/0233014 A1 * | 10/2005 | Lee | A61K 31/198 424/757 |
| 2007/0004623 A1 | 1/2007 | Bellini et al. | |
| 2012/0219667 A1 | 8/2012 | Kelly et al. | |
| 2013/0045273 A1 | 2/2013 | Cuomo et al. | |

FOREIGN PATENT DOCUMENTS

| | | |
|---|---|---|
| WO | WO03088947 | 10/2003 |
| WO | WO2008107909 | 9/2008 |

* cited by examiner

*Primary Examiner* — Chris R Tate
*Assistant Examiner* — Russell Fiebig
(74) *Attorney, Agent, or Firm* — Pate Baird, PLLC

(57) ABSTRACT

A dietary supplement that may include chromium 4-hydroxyisoleucinate. The chromium 4-hydroxyisoleucinate may be provided in a molar ratio between 1:5 and 5:1 ligand to metal. The dietary supplement may be used to manage blood glucose levels, to improve insulin resistance, and to improve glucose uptake.

7 Claims, No Drawings

CHROMIUM 4-HYDROXYISOLEUCINATE COMPOUND METHODS FOR PREPARTION AND USE

RELATED APPLICATIONS

This application claims the benefit of U.S. Provisional Patent Application Ser. No. 61/947,103, filed on Mar. 3, 2014, which is hereby incorporated by reference in its entirety.

BACKGROUND

1. The Field of the Invention

This invention relates to a dietary supplement containing chromium 4-hydroxyisoleucinate, and more particularly to methods for preparing chromium 4-hydroxyisoleucinate and methods for using chromium 4-hydroxyisoleucinate as a blood glucose management tool.

2. Background

Numerous products and procedures are currently available for helping a person manage diabetes. One method for managing diabetes can include lifestyle changes, such as diet and exercise, intended to maintain blood glucose levels within a desired range. Another method for managing diabetes can include various types of medications. These methods can also be used in combination with each other.

Certain products have attempted to utilize the benefits of hydroxylated amino acids in managing diabetes by attempting to increase the effectiveness of certain medications for diabetes. The hydroxylated amino acids are used in combination with some other medication for diabetes. What is needed is a hydroxylated amino acid product that can improve glucose uptake and improve insulin resistance when used in combination with natural products or herbs.

BRIEF SUMMARY OF THE INVENTION

In accordance with the foregoing, certain embodiments of a product, compound and method in accordance with the invention provide an oral product that can be consumed by a person to facilitate and promote the control of blood glucose levels, treat diabetes. The oral product may be suitably formulated to control blood glucose levels in humans.

In one embodiment, the oral product may be formulated as a powder that is mixed with a liquid in preparation for consumption. The resulting beverage may then be consumed by a person or user to maintain blood glucose levels within a desired range. The resulting beverage may be used to improve insulin resistance. The resulting beverage may be used to improve glucose uptake, primarily via glucose transporter type 4 (GLUT4). The resulting beverage may also provide a combination of these benefits.

In a separate embodiment, the oral product may be formulated as a liquid that is ready for consumption. The liquid may then be consumed by a person or user to maintain blood glucose levels within a desired range. The liquid may be used to improve insulin resistance. The liquid may be used to improve glucose uptake, primarily via glucose transporter type 4 (GLUT4). The liquid may also provide a combination of these benefits.

In a separate embodiment, the oral product may be formulated as a gel or gum that is ready for consumption. The gel or gum may then be consumed or chewed by a person or user to maintain blood glucose levels within a desired range. The gel or gum may be used to improve insulin resistance. The gel or gum may be used to improve glucose uptake, primarily via glucose transporter type 4 (GLUT4). The gel or gum may also provide a combination of these benefits.

In a separate embodiment, the oral product may be formulated as a food product that is ready for consumption. The food product may then be consumed by a person or user to maintain blood glucose levels within a desired range. The food product may be used to improve insulin resistance. The food product may be used to improve glucose uptake, primarily via glucose transporter type 4 (GLUT4). The food product may also provide a combination of these benefits.

In a separate embodiment, the product may be administered by a variety of methods, including without limitation, orally, subcutaneously, intravenously, and intramuscularly.

DETAILED DESCRIPTION OF THE PREFERRED EMBODIMENTS

It will be readily understood that the components of the present invention, as generally described herein, could be arranged and designed in a wide variety of different configurations or formulations. Thus, the following more detailed description of the embodiments of the system, product and method of the present invention, is not intended to limit the scope of the invention, as claimed, but is merely representative of various embodiments of the invention.

In one embodiment, the method of preparation, formulation, or chemical synthesis of chromium 4-hydroxyisoleucinate may be described with the following steps. First, two liters (2 L) of water is heated to 60° C.±5° C. Second, 386.2 grams of chromium chloride ($CrCl_2 6H_2O$) is added until dissolved. Third, slowly add 213.4 grams of 4-hydroxyisoleucine followed by adding 570.6 grams of isoleucine with vigorous stirring until everything is dissolved. The liquid may be deep green to light purple in color. The temperature is maintained at 60° C. and the stirring is continued for sixty (60) minutes. After that time, drying can start. After drying, this process may yield approximately one kilogram of chromium 4-hydroxyisoleucinate.

In one embodiment, drying is accomplished by spray drying, although other gentle drying processes can be used. The drying temperature may be between 195° F. and 210° F.

The formula for production of chromium 4-hydroxyisoleucinate, as well as the drying process, can be scaled to any size.

In one embodiment, the method of preparation, formulation, or chemical synthesis of chromium 4-hydroxyisoleucinate is accomplished by using reactants that include at least the following: chromium chloride ($CrCl_2$), chromium nitrite ($Cr(NO_2)$), chromium sulfite ($Cr_3(SO_3)_2$), 4-hydroxyisoleucine, leucine, isoleucine, and valine. The formulation may be carried out in a manner similar to that described previously. For example and not by way of limitation, suitable amounts of the chromium chloride ($CrCl_2$), chromium nitrite ($Cr(NO_2)$), chromium sulfite ($Cr_3(SO_3)_2$) may be dissolved in a suitable amount of water that has been heated to 60° C.±5° C. A suitable amount of 4-hydroxyisoleucine may be added slowly followed by adding suitable amounts of leucine, isoleucine, and valine with vigorous stirring until everything is dissolved. The temperature of the resultant liquid is maintained at 60° C. and the stirring is continued for sixty (60) minutes. After that time, drying can start.

Each of the component/reactants has a respective function, but together they have a separate function. These reactants may be used to produce 20% chromium 4-hydroxyisoleucinate.

The molar ratio for the resulting chromium 4-hydroxyisoleucinate may range from 1:5 to 5:1 ligand to metal. A molar ratio of 3:1 ligand to metal may be considered optimal for many intended uses, although the ratio may be adjusted as desired.

Carriers for a chromium 4-hydroxyisoleucinate product may include the following in a suitable amount for the intended product: maltodextrin, inulin fructooligosaccharides (FOS), and soluble fibers (FOS, GOS, Dextrins, Fibersol, etc.). Other carriers may be possible and still fall within the scope of the invention.

In one embodiment, a chromium 4-hydroxyisoleucinate product may be used in combination with suitable amounts of fenugreek seed, cinnamon, gymnema, syzygium, galactomannan, and/or baobab. Other herbs and additives may be substituted. Other herbs and additives may provide similar benefits, or separate benefits.

The amounts of the respective reactants used to produce the chromium 4-hydroxyisoleucinate product may be adjusted plus or minus 20%. Moreover, the order in which the reactants are utilized may be altered and amended as desired. In separate embodiments, it may be possible to obtain the desired chromium 4-hydroxyisoleucinate without one or more of the listed reactants.

Possible uses for an effective amount of chromium 4-hydroxyisoleucinate may include the following: blood glucose management; improve insulin resistance; and improve glucose uptake, primarily via glucose transporter type 4 (GLUT4).

A product containing chromium 4-hydroxyisoleucinate may be utilized in combination with other known treatments for diabetes. A product containing chromium 4-hydroxyisoleucinate may also help alleviate dependence on insulin, or reduce the amount of insulin appropriate for treating a person with diabetes.

What is claimed and desired to be secured by United States Letters Patent is:

1. A method for producing chromium 4-hydroxyisoleucinate comprising the steps of:
   (a) providing water heated to 60° C.±5° C.;
   (b) dissolving chromium chloride in the water;
   (c) adding 4-hydroxyisoleucine to the water;
   (d) adding isoleucine to the water;
   (e) stirring the water until all the components are dissolved into a mixture;
   (f) maintaining the temperature of the mixture at 60° C.±5° C. while continuing to stir the mixture for approximately sixty (60) minutes; and
   (g) drying the mixture to obtain the chromium 4-hydroxyisoleucinate.

2. The method of claim 1 further comprising dissolving chromium nitrite in the water after dissolving the chromium chloride.

3. The method of claim 1 further comprising dissolving chromium sulfite in the water after dissolving the chromium chloride.

4. A method for producing chromium 4-hydroxyisoleucinate comprising the steps of:
   (a) providing water heated to 60° C.±5° C.;
   (b) dissolving chromium chloride in the water;
   (c) dissolving chromium nitrite in the water;
   (d) dissolving chromium sulfite in the water;
   (e) adding 4-hydroxyisoleucine to the water;
   (f) adding isoleucine to the water;
   (g) adding leucine to the water;
   (h) adding valine to the water;
   (i) stirring the water until all the components are dissolved into a mixture;
   (j) maintaining the temperature of the mixture at 60° C.±5° C. while continuing to stir the mixture for approximately sixty (60) minutes; and
   (k) drying the mixture to obtain the chromium 4-hydroxyisoleucinate.

5. A method for producing chromium 4-hydroxyisoleucinate comprising the steps of:
   (a) providing approximately two liters (2 L) of water heated to 60° C.±5° C.;
   (b) dissolving approximately 386.2 g of chromium chloride in the water;
   (c) adding approximately 213.4 g of 4-hydroxyisoleucine to the water;
   (d) stirring the water until all the components are dissolved into a mixture;
   (e) maintaining the temperature of the mixture at 60° C.±5° C. while continuing to stir the mixture for approximately sixty (60) minutes; and
   (f) spray-drying the mixture at a temperature between 195° F. and 210° F. to obtain the chromium 4-hydroxyisoleucinate.

6. The method of claim 5 wherein the resultant chromium 4-hydroxyisoleucinate has a molar ratio from about 1:5 to 5:1 ligand to metal.

7. The method of claim 5 wherein the resultant chromium 4-hydroxyisoleucinate has a molar ratio of approximately 3:1 ligand to metal.

* * * * *